United States Patent [19]

Laughlin et al.

[11] Patent Number: 4,589,419
[45] Date of Patent: May 20, 1986

[54] CATHETER FOR TREATING ARTERIAL OCCLUSION

[75] Inventors: Donald E. Laughlin, West Branch; Robert F. Wilson; Thomas A. Drews, both of Iowa City, all of Iowa

[73] Assignee: University of Iowa Research Foundation, Iowa City, Iowa

[21] Appl. No.: 667,130

[22] Filed: Nov. 1, 1984

[51] Int. Cl.$^4$ ............................................. A61B 10/00
[52] U.S. Cl. ................................................... 128/663
[58] Field of Search ............................ 128/663, 661; 604/96–99, 101; 73/861.25

[56] References Cited

U.S. PATENT DOCUMENTS 4,354,500 10/1982 Colley et al. ..................... 128/663
4,355,643 10/1982 Laughlin et al. .................. 128/663

OTHER PUBLICATIONS

Nealeigh, R. C. et al, "A Venous Pulse Doppler Catheter-Tip Flow-Meter for Measuring . . . Arteries", Proc. 12th Ann. R.M. Bioengr. Symp., Denver, Colorado, Apr. 28–30, 1975, pp. 7–10.
Cole, J. S. and Hartley, C. J.: The Pulsed Doppler Coronary Artery Catheter Circulation, 56: 18, 1977.
Hartley, Cole: A Single Crystal Ultrasonic Catheter-Tip Velocity Probe, Medical Instrumentation, 8: 241-3, 1974.
Coppess, Young, White, Laughlin: An Ultrasonic Pulsed Doppler Balloon Catheter for Use in Cardiovascular Diagnosis, Bio. Med. Sci. Instr., 19: 9, 1983.

Primary Examiner—Kyle L. Howell
Assistant Examiner—Francis J. Jaworski
Attorney, Agent, or Firm—Ferris M. Stout

[57] ABSTRACT

The cardiac catheter of this invention combines in a single, thin tube, an acoustic transducer for determining blood flow velocity, and a separate lumen with a removable, flexible, radio-opaque guide wire, enabling the surgeon to locate the site of arterial blockage, evaluate the blockage, and assess the effect of the treatment.

4 Claims, 3 Drawing Figures

CATHETER FOR TREATING ARTERIAL OCCLUSION

The research project which led to this invention was funded by the National Institutes of Health, Contract Numbers SHL-27633, SHL-14388, and SHL-29976; and the Veterans Administration, MRIS 1180.2.

BACKGROUND OF THE INVENTION

Physicians prefer to treat patients suffering from coronary artery blockage without resort to open heart surgery. This can be accomplished by threading a guide catheter up a large artery to and into the aorta, and down the aorta to the ostium (the opening) of the coronary artery. Next the surgeon inserts a smaller catheter into the guide catheter, and manoeuvers it into and down the coronary artery and its branches to the site of stenosis (arterial blockage). The smaller catheter may have a fine, coiled guide wire in it with which the surgeon can manoeuver the catheter through arterial forks in the network of arteries around the heart. Once the catheter is in place, drugs are injected up the small catheter to treat the stenosis; or a balloon on the end of the catheter is inflated, increasing the arterial lumen available for blood flow (angioplasty).

A surgeon employing this procedure needs to know that he has reached the stenosis which is causing the patient's distress. If the blockage site he has reached is of intermediate severity (10% to 90% obstruction of the lumen), it can be difficult for him to tell if the stenosis he has reached actually impedes blood supply to the heart. Experimental attempts have been made to deal with this problem with a Doppler acoustic transducer fastened to the end of the catheter. The transducer signal, suitably amplified, measures the blood flow velocity through the artery.

A catheter which measures blood flow velocity must be small enough in diameter not itself to restrict the flow of blood through the artery. On the other hand the size limitation makes it difficult to wire the transducer into the catheter. Until the present invention it has not been practical to include a steering wire in the catheter which carries the transducer. Presently available catheters cannot measure flow velocity beyond the coronary artery ostium and are not of significant use in measuring the physiological significance of coronary artery narrowing, or measuring changes in flow velocity in individual coronary arteries. Moreover the location of the transducer on the end of the catheter means that it is subject to occlusion by the arterial wall, so that signal stability over a useful time interval is unreliable.

Hence there exists a need for a catheter thin enough to enter the coronary arteries, having a reliable Doppler acoustic transducer near its distal end, a lumen separated from the conductive wires of the transducer, and a steering wire in the lumen which can be removed so that therapeutic means can be introduced through the catheter to the blockage site.

SUMMARY OF THE INVENTION

The catheter of this invention enables measurement of the physiological significance of a coronary stenosis, assessment of the treatment of the stenosis, and if necessary retreatment, all with a single insertion of the catheter.

The catheter is only one millimeter in diameter. It can be readily manipulated (via the steering wire) past forks in the coronary arteries. Moreover the catheter allows sufficient blood to flow past it to enable reliable blood velocity readings in coronary arteries of moderate size without obstructing maximal blood flow. The surgeon can steer this catheter into the ostium of the coronary artery, past forks in the artery, and up to the suspected stenosis. Once in place, the surgeon administers a drug which dilates the small arteries around the heart which, without the drug, resist and limit flow through the coronary artery. Flow through a patent coronary artery will suddenly increase four or five fold when the small arteries dilate. If the flow increase is substantially less than this, the surgeon concludes that his catheter is located at the source of trouble, and he proceeds with the treatment.

The catheter is lengthwise divided into two compartments. The upper compartment accommodates two insulated wires which energize a tiny transducer fixed in the outer wall of the catheter about a centimeter from its distal end. The lower compartment contains the steering wire. Once the catheter is threaded into place, the steering wire is withdrawn, and drugs are pumped into and through the lower compartment to the site of the blockage. The transducer, continuously monitoring blood flow rate through the artery, provides immediate information on the flow response to drugs or effectiveness of the treatment.

DRAWINGS

FIG. 1: Longitudinal section through the catheter

FIG. 2: Section through transducer at Section A—A' of FIG. 1.

FIG. 3: Doppler acoustic transducer, enlarged, viewed from the back.

A PREFERRED EMBODIMENT

Referring to FIG. 1, a catheter (1) having an outside diameter of one millimeter (three French, in the language of the trade) is divided by a longitudinal septum (2) into an upper lumen (3) and a lower lumen (4). Two insulated wires (5) and (5') extend the length of the catheter inside the upper lumen (2).

About one centimeter from the distal end of the catheter a vee-shaped notch (6) is cut through the upper lumen 2, at an angle of about 45 degrees from the plane normal to the catheter. A dab of conductive epoxy (7) electrically connects and mechanically fixes a 20 megahertz acoustic crystal transducer (8) against the distal surface of notch (6). Finally, the notch, the crystal, the wires in the upper lumen, and part of the distal end of upper lumen (3) are encapsulated in a body-compatible and acoustically transparent epoxy cement (9).

Figure 1:
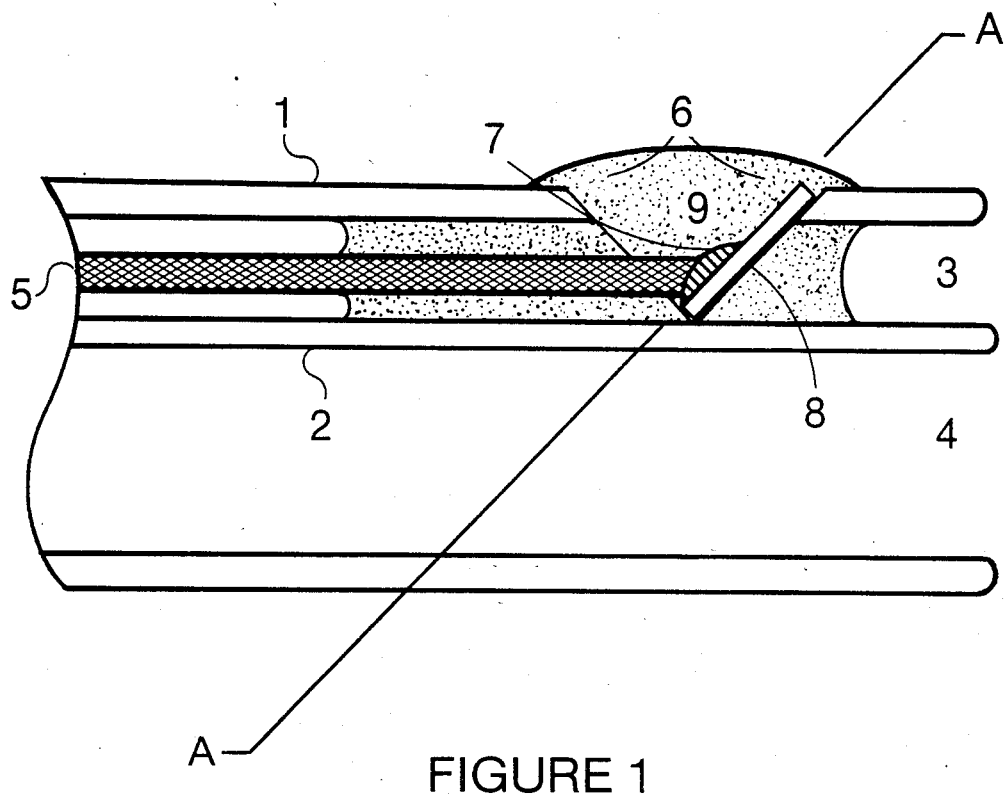
Figure 2:
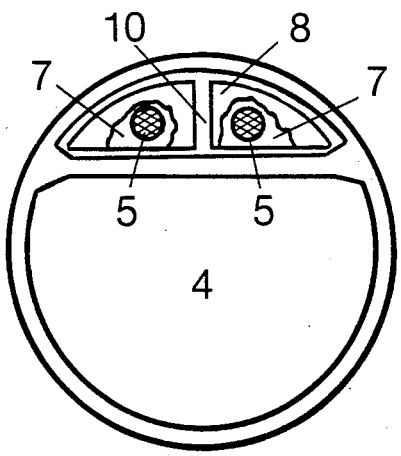
FIG. 2 shows a section of the catheter through the gold-plated surface of the transducer, that is, through A—A' of FIG. 1, looking toward the distal end of the catheter. It is somewhat clearer in this view how conductive epoxy (7) connects wires (5) and (5') to the transducer (8).
Figure 3:
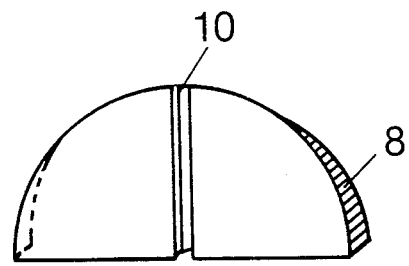
FIG. 3 shows the gold-plated side of a 20 mhz acoustic crystal transducer (8), cut as shown to fit against the side of notch (6). Groove (10) divides the gold plating on the back of the crystal into two electrically distinct areas which serve as electrodes for connection to the wires (5) and (5').

In an alternative embodiment, the crystal is soldered to the wires with 40/60 soft solder. In another alternate embodiment the conduction wires are embedded in the catheter when it is made. In yet another alternative embodiment, the transducer is fastened to the distal-facing surface of the notch.

The terms and descriptions recited herein are exemplary of the invention. They are not to be considered as defining or limiting the invention, which is as set forth in the claims.

What is claimed is:

1. In the method for treating blockage of a coronary artery in which a catheter is threaded up to the site of the blockage by following a radio-opaque guide wire in the catheter flouroscopically, the improvement comprising the steps of determining the rate at which blood is flowing in the artery by means of a single-crystal Doppler transducer embedded in the side of the catheter near its distal end, administrating a vasodilator, and determining from the subsequent change in blood flow velocity measured by the Doppler transducer whether the artery downstream of the transducer is patent.

2. In a cardiac catheter of the type having more than one lumen, electrically conductive wires in one of the lumens, and in another lumen a radio-opaque guide wire, the improvement which comprises a single-crystal doppler transducer mounted on the side of the catheter near its distal end and at an acute angle to the longitudinal axis of the catheter at the mounting site of the transducer, connected to the wires in the lumen.

3. A catheter having a longitudinal wall, the wall defining a longitudinal lumen, and a proximal and a distal end, electrically conductive wires embedded in the wall of the catheter, and a single-crystal Doppler transducer affixed in the wall of the catheter at an acute angle to the longitudinal axis of the catheter at the mounting site of the transducer near its distal end.

4. The catheter of claim 2 further comprising a longitudinal septum in the lumen of the tube dividing the lumen into an upper and a lower lumen.

* * * * *